United States Patent [19]

Hüschelrath et al.

[11] Patent Number: 4,480,477
[45] Date of Patent: Nov. 6, 1984

[54] ELECTRODYNAMIC INSTRUMENT TRANSFORMER HEAD

[75] Inventors: Gerhard Hüschelrath, Laufach-Frohnhofen; Ewald Kowol, Wehrheim; Ursula Orthen, Hanau, all of Fed. Rep. of Germany

[73] Assignee: Nukem GmbH, Hanau am Main, Fed. Rep. of Germany

[21] Appl. No.: 387,148

[22] Filed: Jun. 10, 1982

[30] Foreign Application Priority Data

Jun. 16, 1981 [DE] Fed. Rep. of Germany ....... 3123935

[51] Int. Cl.³ ............................................. G01N 29/04
[52] U.S. Cl. ....................................... 73/643; 336/212
[58] Field of Search ........................... 73/643; 336/212

[56] References Cited

U.S. PATENT DOCUMENTS 3,555,887  1/1971  Wood ..................................... 73/643

FOREIGN PATENT DOCUMENTS 376127  5/1973  U.S.S.R. ................................. 73/643

Primary Examiner—Anthony V. Ciarlante
Attorney, Agent, or Firm—Cushman, Darby & Cushman

[57] ABSTRACT

An electrodynamic instrument transformer head (10) for the non-destructive testing of materials by means of ultrasonics has a pole shoe (20) provided with exciting and receiving coils (14, 16), said pole shoe comprising a slotted end section (24) to prevent a formation of eddy currents. The end section (24) thereby is continuing into a basic body (22) preferably being made of a different material.

8 Claims, 2 Drawing Figures

ELECTRODYNAMIC INSTRUMENT TRANSFORMER HEAD

This invention relates to an electrodynamic instrument tranformer head for a non-destructive testing of materials by means of ultrasonics, comprising a pole show being aligned relative to an electroconductive, ferromagnetic work piece to be tested, and an exciting coil and a receiving coil.

In the non-destructive testing of material by means of ultrasonics, piezoelectric oscillators have proved good, where the ultrasonic waves emanating from said oscillators are introduced into the work piece by means of a coupling means like e.g. water. However, the use of such piezoelectric oscillators is limited in such cases where the coupling means is submitted to quick and substantial thermal variations, for example. By means of the electrodynamic sound transformers a contact-free testing of material with ultrasonics is rendered possibile, without having to make lower demands on them with regard to testing accuracy as compared to the piezoelectric oscillators.

The electrodynamic generation of ultrasonics in electroconductive means is based on the interaction of eddy currents with static magnetic fields, whereby a particle movement, hence the ultrasonic waves, are generated in the work piece. Here the required magnetic field is generated preferably by an electromagnet via a desired pole shoe configuration. By high-frequency currents carried in the wires of the exciting coil, eddy currents are then generated in the work piece, of which the depth of impression is contingent on the frequency used.

Electrodynamic sound transformers are described e.g. in the German specification No. 26 21 684 or the German disclosure No. 29 44 819. Both literature references deal with the special configuration of the pole shoe in order to enable a good signal evaluation of the pulses taken by the receiving coil. To this end, the German specification No. 26 21 684 suggests to design a magnet core of an electromagnet in such a manner that it will continuously taper off to the surface of the work piece. By this design, however, it is not guaranteed that a feed-back coming from the work piece to be tested and the resulting generation of eddy currents in the magnet core will be eliminated in such a manner that a resolution of test signals can take place, which will enable a detecting of even the smallest defects in the work piece. By a special composition of matter of the magnet according to the German disclosure No. 29 44 819, a respective generation of eddy current in the yoke of the electromagnet shall be reduced. To this end it is suggested to make the core of the electromagnet, at least partially, of composite material, which essentially consists of powdered iron and an elastic binding agent. By using ferrites, however, there are limits with regard to the strength of the magnetic field. Also the manufacture of appropriate cores is rather expensive, and especially then, if the cores are only partially made of this composite material, it is not guaranteed that cores of the same dimensions will also lead to the same magnetic fields.

It is the object of the present invention to develop an electrodynamic instrument transformer head of the kind as mentioned at the outset in such a manner that the generation of ultrasonic signals in the pole shoe, caused by a feedback from the work piece to be tested and the resulting formation of eddy currents, is suppressed in such a manner that the signals to be taken from the receiving coil will enable a simple evaluation and a good resolution.

According to the invention this problem is solved in that the pole shoe holding the coils is composed of a basic body and an end section being provided with radially extending slots. By the design of the slots it is guaranteed that a formation of eddy currents in the pole shoe is stopped, so that the test signals will not be exposed to undesired influences coming from the electromagnet. By composing the pole shoe of a basic body and an end section, which can be made separately, there is the further advantage that the end section can be of any design whatsoever without having to make the electromagnet with pole shoes specifically in adaptation thereto. The arrangement of the slots further offers the advantage that the pole shoe surface facing the work piece is reduced, thus resulting in an intensification of the magnetic field, whereby the pulses registered by the receiving coil in their turn enable a better evaluation of the signals.

According to an embodiment of the invention, the basic body and the end section are built up of different materials, where the basic body preferably is made of cobalt iron and the end section of stainless steel 350 or stainless steel 370 (herein after St 350 and 370). The use of cobalt iron offers the advantage that the largest possible magnetic field with respect to the electromagnet data is made available since the highest available saturation induction is obtained. As the - likewise ferromgnetic - end section consists of St 350 or St 370, it is guaranteed at the same time that a disturbing noise coming from the cobalt iron cannot occur in the range of the coils.

In order not to disturb the continuity of the flux distribution by the arrangement of the slots, according to an especially preferably embodiment of the invention one places insulated transformer sheets in the slots, so that the cross-section surface of the end section facing the work piece is even.

An intensification of magnetic field, thus an increase of induction in the end section facing the work piece to be tested, can in addition be obtained by a tapering in direction of the work piece. The end section will preferably be designed as a truncated cone.

According to another embodiment of the invention, the pole shoe is an inner pole shoe of a magnet yoke, being concentrically surrounded by an outer pole shoe of essentially hollow-cylindrical configuration, which outer pole shoe preferably will include two edge zones arranged diametrically to each other and inclined at an angle against the inner pole shoe. In a preferred manner, the outer surfaces of the edge sections facing the work piece are thereby arranged on the same plane or almost the same and have circular recesses, of which the centers of curvature are within the range of the inner pole shoe and preferably on the center axis of said pole shoe. In other words, in sectional view the magnet yoke is M-shaped, of which the outer leg is squared off inwards.

By such a shaping of the magnet yoke, especially of the squared off sections, an additional advantage is achieved consisting therein that the magnetic resistance is reduced. By that means, the measurings detected with the electrodynamic transformer according to the invention will become to a far extent independent of the actual value of the relative permeability of the work piece. The material of the outer legs including their squared-off sections can likewise be St 350 or St 370.

Further details, advantages and characteristics of the invention can be learned from the preferred embodiment example shown in the attached drawings wherein FIG. 1 is a side view in elevation and FIG. 2 is a top plan view of the device of the present invention.

Figure 1:
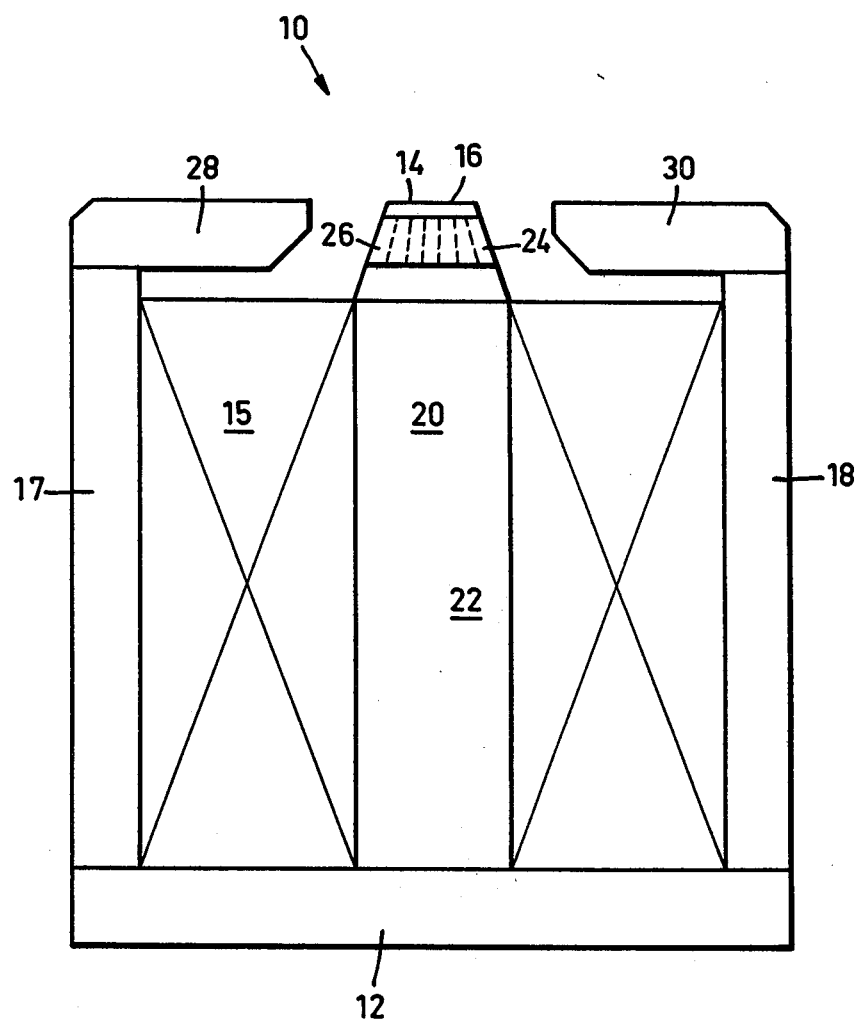
FIG. 1 is side view in elevation of an embodiment of the present invention.
Figure 2:
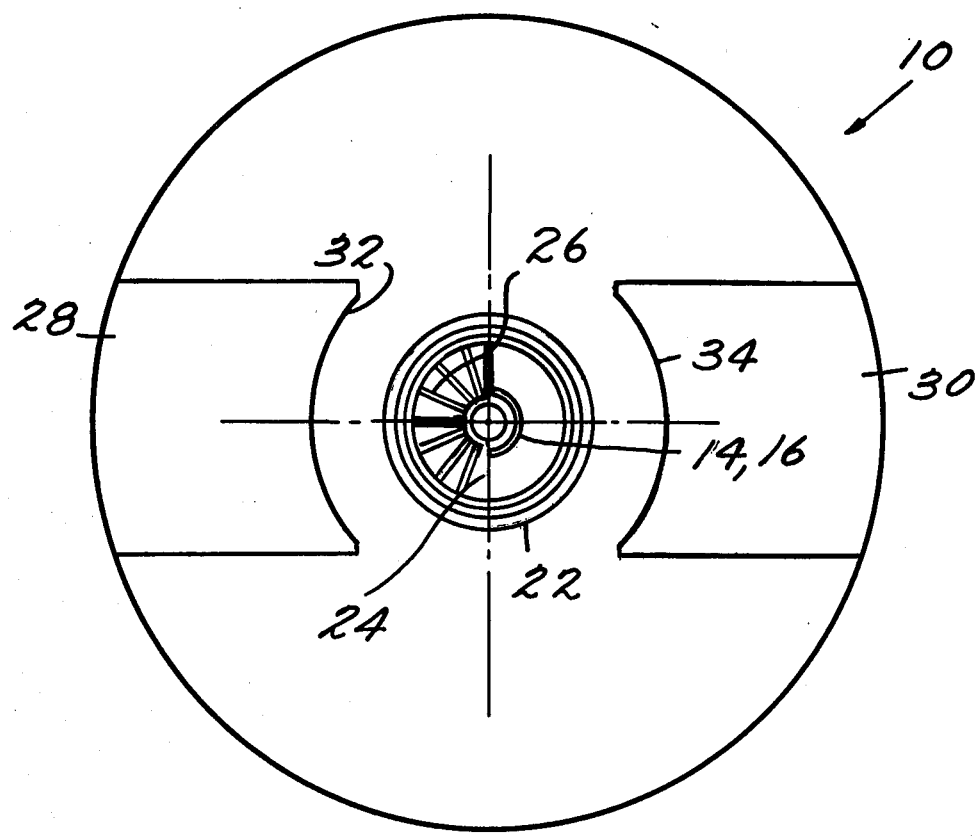
FIG. 2 is a top plan view thereof.

The Figure shows the longitudinal section of an electrodynamic instrument transformer head 10, being essentially composed of an electromagnet 12, and exciting coil 14 and a receiving coil 16. The electromagnet 12 has a magnetizing coil 15 as well as a magnet yoke being M-shaped in sectional view. The magnet yoke comprises an inner pole shoe 20 of rotational-symmetric configuration, being concentricly surrounded by the outer pole shoe of hollow-cylindrical configuration, indicuted through its legs 17 and 18 in the sectional view. On the free end of the inner pole shoe 20 the actual transformer is arranged, being composed of the exciting coil and the receiving coil 14 or, resp. 16, and which is vertically interspersed with the magnetic flux generated by magnet 12. The number of turns of the coils 14 and 16 are determined by the electric requirements, hence the transmitting coil 14 regarding its number of turns must be adapted to the resistance of the generator, and the number of turns of the receiving coil 16 as to the winding capacity must meet the highest frequency coming up. The electromagnet 12 is preferably excited by direct current, intermittent direct current or by an alternating current of low frequency, in which manner, among others, cooling problems can be eliminated.

According to the invention, the inner pole shoe 20 is composed of two sections, i.e. a basic body 22 being connected to the outer pole shoe, and an end section 24 on which the coils 14 and 16 are arranged. The basic body 22 and the end section 24 are preferably made of different materials. Thus the basic body 22 can consist of cobalt iron and the likewise ferromagnetic end section 24 of St 350 or, resp. St 370. Taking cobalt iron as material for the basic body 22 has the advantage that high field strengths are generated without any disturbing noise being transmitted to the coils 14 and 16.

In order to eliminate the formation of eddy currents in the inner pole shoe 20 which could generate ultrasonic signals in said pole shoe and would lead to a reduced measuring accuracy of the electrodynamic transformer head 10, the end section 24 is provided with radially extending slots 26. In these slots preferably insulated transformer sheets can be placed in order to make the free surfaces of the end section 24 even, thus guaranteeing a uniform distribution of flux. Preferably the end section 24 is tapering off in direction to a work piece (not shown), thus it can be shaped like a truncated cone, in order to cause an increase of field strength in the range of the coils 14 and 16.

In order to reduce the magnetic resistance, the outer pole shoe is of a special design to the effect that it has squared off edge regions 28 and 30 diametrically facing each other, and extending in the direction of the end section 24 on one plane. In addition they are provided with circular recesses which concentricly surround the end section 24, where the centers of curvature of the individual recesses are preferably positioned on the axis of the inner pole shoe 20 of rotational-symmetric configuration. The free surfaces of the squared off edge regions or, resp. sections 28 and 30 further are preferably arranged approximately in the plane of the coils 14 and 16. By this design of the outer pole shoe of the electromagnet, the measurings will become independent to a far extent of the actual value of the relative permeability.

By means of the electrodynamic instrument transformer head 10 according to the invention one can test without any difficulty the size or, resp. wall thickness of tubes, rod bars, billets and sheets, from approx. 5 mm even up to 45 mm. The accuracy of measurement can be compared to that of a 2-mc/s piezoelectric oscillator at transverse waves, and ranges between 10 micrometers and 100 micrometers, according to the wall thickness-measuring range and testing and environmental conditions. however, accuracy can still be increased by the evaluation of multiple echoes.

The generation and the evaluation of the signals transmitted and received by the coils, as well as the generation of the magnetic field take place by means of conventional electronic units, which will not be described in more detail in this context. In addition it should be mentioned that the leads to the coils 14 and 16 can be led through a channel being arranged in the center of the inner pole shoe 20.

We claim:

1. An electrodynamic transducer head for the nondestructive testing of materials by means of ultrasonic energy, comprising an electromagnet having a magnet yoke with outer and inner pole shoes, said outer pole shoes surrounding said inner pole shoe, an exciting coil and a receiving coil, said coils being disposed in an area that, in use, faces the work piece being tested, said area being located on the end section of said inner pole shoe, said end section having generally radially extending slots and said end section being tapered in the direction of the work piece to be tested and having the shape of a truncated cone.

2. An electrodynamic transducer head according to claim 1, whereby said magnet yoke has a basic body and said basic body and said end section are made of different materials.

3. An electrodynamic transducer head according to claim 2, whereby said basic body is made of cobalt iron and said end section is made of stainless steel 350.

4. An electrodynamic transducer head according to claim 2, whereby said basic body is made of cobalt iron and said end section is made of stainless steel 370.

5. An electrodynamic transducer head according to claim 1, whereby insulated transformer sheets are placed in said slots.

6. An electrodynamic transducer head for the nondestructive testing of materials by means of ultrasonic energy, comprising an electromagnet having a magnet yoke with outer and inner pole shoes, said outer pole shoes surrounding said inner pole shoe, an exciting coil and a receiving coil, said coils being disposed in an area that, in use, faces the work being tested, said area being located on the end section of said inner pole shoe, said end section having generally radially extending slots, said inner pole shoe being partially concentrically surrounded by said outer pole shoes of hollow-cylindrical configuration, said outer pole shoes comprising two edge sections being arranged diametrically to each other and squared off in the direction facing the inner pole shoe.

7. An electrodynamic transducer head according to claim 6, whereby the outer surfaces of said edge sections facing the work piece are positioned essentially on the same plane and are circularly recessed facing each other, of which the centers of curvature are co-incident with said inner pole shoe.

8. An electrodynamic transducer head according to claim 6 or claim 7, whereby said centers of curvature are positioned on the axis of said inner pole shoe of rotationaly-symmetric configuration.

* * * * *